United States Patent
Kitano et al.

(10) Patent No.: US 11,492,652 B2
(45) Date of Patent: Nov. 8, 2022

(54) METHOD AND KIT FOR ASSESSING POSSIBILITY OF CANCERIZATION

(71) Applicant: TOPPAN PRINTING CO., LTD., Taito-ku (JP)

(72) Inventors: Shiro Kitano, Taito-ku (JP); Kei Tsukamoto, Taito-ku (JP); Shinji Irie, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 757 days.

(21) Appl. No.: 16/165,074

(22) Filed: Oct. 19, 2018

(65) Prior Publication Data

US 2019/0048387 A1 Feb. 14, 2019

Related U.S. Application Data

(63) Continuation of application No. PCT/JP2017/015808, filed on Apr. 19, 2017.

(30) Foreign Application Priority Data

Apr. 19, 2016 (JP) ............................. JP2016-083949

(51) Int. Cl.
*C12Q 1/02* (2006.01)

(52) U.S. Cl.
CPC ........... *C12Q 1/02* (2013.01); *G01N 2800/50* (2013.01); *G01N 2800/7014* (2013.01); *G01N 2800/7028* (2013.01)

(58) Field of Classification Search
CPC .............................................. G01N 2800/7028
See application file for complete search history.

(56) References Cited

U.S. PATENT DOCUMENTS

| | | | |
|---|---|---|---|
| 2010/0196426 A1 | 8/2010 | Skog et al. | |
| 2010/0255528 A1 | 10/2010 | Zudaire et al. | |
| 2013/0236879 A1 | 9/2013 | Berry et al. | |
| 2017/0216498 A1 | 8/2017 | Kang et al. | |

FOREIGN PATENT DOCUMENTS

| | | |
|---|---|---|
| CN | 106039409 A | 10/2016 |
| JP | 2010-098958 A | 5/2010 |
| JP | 2011-510663 A | 4/2011 |
| JP | 2012-115254 A | 6/2012 |
| WO | WO 02/20729 A2 | 3/2002 |
| WO | WO 2014/035668 A1 | 3/2014 |

OTHER PUBLICATIONS

Beckham et al., The J of Urology, 2014, 192:583-592.*
Sheldon et al., Blood, 116(13):2385-2394.*
Office Action dated Jul. 13, 2020 in corresponding European Patent Appiication No. 17 786 014.5, 7 pages.
Chun-Yen Liu et al., "Control of Vascular Network Location in Millimeter-sized 3D-tissues by Micrometer-sized Collagen Coated Cells", Biochemical and Biophysical Research Communications, vol. 472, No. 1, Feb. 23, 2016, pp. 131-136.
Extended European Search Report dated Nov. 5, 2019 in corresponding European Patent Application No. 17786014.5, 8 pages.
International Search Report dated Jul. 25, 2017 in PCT/JP 2017/015808, filed Apr. 19, 2017, 5 pages.
Yukawa et al., "Influence of cryopreservation of exosomes derived from liver cancer cells on angiogenic potency", Organ Biology, vol. 21, No. 2, 2014, pp. 237-240 (with English abstract).
Yi et al., "High-grade ovarian cancer secreting effective exosomes in tumor angiogenesis", International Journal of Clinical and Experimental Pathology, 2015, 8(5), pp. 5062-5070.
Antonyak et al., "Microvesicles as Mediators of Intercellular Communication in Cancer", Methods in Molecular Biology, vol. 1165, 2014, pp. 147-173.
Melo et al., "Glypican-1 identifies cancer exosomes and detects early pancreatic cancer", Nature, vol. 523, 2015, 24 pages.
Hoshino et al., "Tumour exosome integrins determine organotropic metastasis", Nature, vol. 527, 2015, 19 pages.
Mulvey et al., "Extracellular vesicle-mediated phenotype switching in malignant and non-malignant colon cells", BMC Cancer, 15:571, 2015, p. 1-14.
Ribeiro et al., "Exosomes Function in Pro- and Anti-Angiogenesis", NIH Public Access Author Manuscript, Curr Angiogenes. 2(1), 54-59, 2013, 13 pages.
Office Action dated Feb. 24, 2022 in corresponding Chinese Patent Application No. 201780023935.3 (with English-language Transiation), 10 pages.
Carla J. Beckham, et al., Bladder Cancer Exosomes Contain EDIL-3/Del1 and Facilitate Cancer Progression, The Journal of Urology, vol. 192, No. 2, pp. 583 to 592, published on Aug. 31, 2014.
Helen Sheldon, et al., New mechanism for Notch signaling to endothelium at a distance by Delta-like 4 incorporation into exosomes, Vascular Biology, vol. 116, No. 3, pp. 2385 to 2394, published on Sep. 30, 2010.
Office Action dated Sep. 3, 2021 in corresponding Chinese Patent Application No. 201780023935.3 (with English-language Translation), 8 pages.

* cited by examiner

*Primary Examiner* — Bin Shen
(74) *Attorney, Agent, or Firm* — Oblon, McClelland, Maier & Neustadt, L.L.P.

(57) ABSTRACT

A method of assessing a possibility of cancerization including culturing a cell structure including normal cells and having a vascular network structure in a presence of a biological specimen from a subject, and assessing a possibility of cancerization in the subject based on a state of vessels in the cell structure after the culturing. The biological specimen is a body fluid specimen from the subject, a cell extract of cells from the subject, or a culture supernatant of cells from the subject, and the possibility of cancerization is assessed as high in the subject when a number of cells forming the vessels in the cell structure is larger than a number of cells cultured in an absence of the body fluid specimen, or when the vascular network structure in the cell structure extends.

20 Claims, 2 Drawing Sheets

METHOD AND KIT FOR ASSESSING POSSIBILITY OF CANCERIZATION

CROSS-REFERENCE TO RELATED APPLICATIONS

The present application is a continuation of International Application No. PCT/JP2017/015808, filed Apr. 19, 2017, which is based upon and claims the benefits of priority to Japanese Application No. 2016-083949, filed Apr. 19, 2016. The entire contents of these applications are incorporated herein by reference.

BACKGROUND OF THE INVENTION

Field of the Invention

The present invention relates to a method and kit for assessing the possibility of cancerization in a subject by using a cell structure formed from normal cells and including a vascular network structure.

Discussion of the Background

In recent years, biomarker investigation has been actively performed using liquid biopsy for early detection and prediction of malignancy and metastasis of cancer.

Typical biomarkers in liquid biopsy include, for example, proteins, nucleic acids (for example, ccfDNA, microRNA, and others), circulating tumor cells (CTCs), extracellularly secreted vesicles (exosomes), and others. Among them, exosomes have been increasingly studied in recent years as a biomarker that is deeply involved with various stages of diseases typified by cancer such as the occurrence, malignancy, progression, and metastasis.

Exosomes are membrane vesicles with a diameter approximately in the range of 40 nm to 150 nm that are secreted by most cells.

In vivo, exosomes are observed in body fluids such as saliva, blood, urine, amniotic fluid, and malignant ascites, and are secreted by cultured cells as well. It has been pointed out in recent years that there is a possibility that exosomes play the role of signaling to distant cells and tissues. Exosomes contain various proteins, lipids, and nucleic acids, and possibly are conveyed to other cells to bring about functional changes and physiological changes. Specifically, it has been suggested that exosomes have a function of mediation of adaptive immune responses to infectious agents and tumors, tissue repair, neural transmission, conveyance of pathogenic proteins, and others.

Recent researches have revealed that subsets of microRNA included in exosomes vary depending on the tumor cell species secreting these subsets. In addition, the protein called glypican 1 (GPC1) has been discovered specifically included in exosomes derived from a cancer patient (pancreas cancer). It has been suggested that the nucleic acids and proteins included in exosomes would provide useful information for cancer early detection, prognosis, and disease state monitoring (for example, refer to NPL 1).

It has also been reported that exosomes would be deeply involved in metastasis and malignancy of cancer (angiogenesis and growth efficiency improvement) (for example, refer to NPLs 2 to 4).

NPL 1: Sonia A. M., et al., "Glypican-1 identifies cancer exosomes and detects early pancreatic cancer", NATURE, vol. 523, p 177-182, 2015

NPL 2: Ayuko H., et al., "Tumour exosome integrins determine organotropic metastasis", NATURE, vol. 527, p 329-335, 2015

NPL 3: Hillary E. M., et al., "Extracellular vesicle-mediated phenotype switching in malignant and non-malignant colon cells", BMC Cancer, 15:571, p 1-14, 2015

NPL 4: Mara F. R., et al., "Exosomes Function in Pro- and Anti-Angiogenesis", NIH-PA, 2(1), p 54-59, 2013

SUMMARY OF THE INVENTION

According to an aspect of the present invention, a method of assessing a possibility of cancerization includes culturing a cell structure including normal cells and having a vascular network structure in a presence of a biological specimen from a subject, and assessing a possibility of cancerization in the subject based on a state of vessels in the cell structure after the culturing. The biological specimen is a body fluid specimen from the subject, a cell extract of cells from the subject, or a culture supernatant of cells from the subject, and the possibility of cancerization is assessed as high in the subject when a number of cells forming the vessels in the cell structure is larger than a number of cells cultured in an absence of the body fluid specimen, or when the vascular network structure in the cell structure extends.

According to another aspect of the present invention, a kit for assessing a possibility of cancerization includes a cell culture vessel, and a cell structure which has a vascular network structure and includes normal cells formed on the cell culture vessel.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
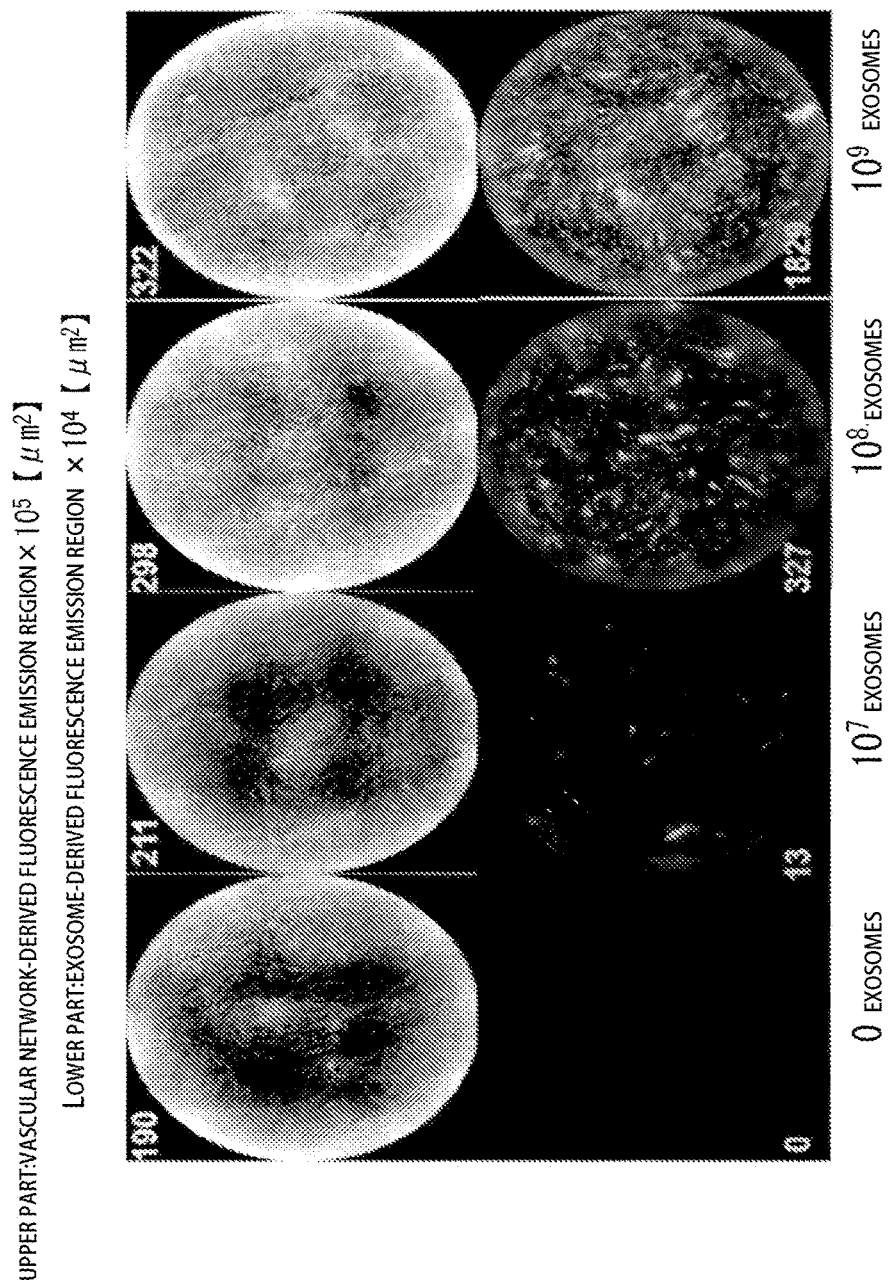
FIG. 1 is an image of vascular network-derived fluorescence emission regions and exosome-derived fluorescence emission regions in which the numbers of added exosomes are 0, $1 \times 10^7$, $1 \times 10^8$, and $1 \times 10^9$ in Example 1.

The embodiments will now be described with reference to the accompanying drawings, wherein like reference numerals designate corresponding or identical elements throughout the various drawings.

«Method of Assessing the Possibility of Cancerization in a Subject»

A method of assessing the possibility of cancerization according to an embodiment of the present invention is a method of assessing the possibility of cancerization including: a culture step of culturing a cell structure formed from normal cells and including a vascular network structure in the presence of a biological specimen derived from a subject; and an assessment step of assessing a possibility of cancerization in the subject using the state of vessels in the cell structure after the culture step as an index. When the subject has cancer, a biological specimen derived from the subject includes a cancer factor such as microRNAs secreted by cancer cells. In the method according to the present embodiment, it is evaluated whether the biological specimen includes a cancer factor by investigating the influence on the vascular network structure formed from normal cells, thereby to assess the possibility of cancerization in the subject based on the evaluation.

According to the method of the present embodiment, it is not necessarily required to perform a biopsy of cancer tissue but the possibility of cancerization can be assessed by using a body fluid specimen that can be taken in a less invasive manner. In addition, the possibility of cancerization can be assessed in a simpler manner without the need for gene analysis. Exosomes in particular are used for early detection of cancer as well. Accordingly, the method according to the present embodiment can be expected to apply to diagnostic techniques for early detection of primary cancer and recurrent cancer.

In general, "exosomes" are membrane vesicles with a diameter in the range of 40 nm to 150 nm secreted by various cells. It is known that the membrane vesicles include nucleic acids such as miRNA and mRNA, proteins, lipids, and others. The exosomes secreted by cancer cells include microRNAs and proteins involved in cancerization, and thus when a cell structure formed from normal cells is cultured in the presence of exosomes secreted by cancer cells, the cells constituting the cell structure also become cancerated.

The method according to the present embodiment will be described below in detail.

<Cell Structure>

In the present embodiment and the present specification, the "cell structure" is a three-dimensional structure in which multiple cell layers are laminated. The cell structure for use in the present embodiment (hereinafter, also called "cell structure according to the present embodiment") includes a vascular network structure and is composed of endothelial cells that constitute vessels and cells that do not constitute vessels (cells other than the endothelial cells). That is, the cell structure according to the present embodiment is a structure in which a vascular network structure of lymph vessels and/or blood vessels is three-dimensionally formed in a cell laminate in which vessels are not formed, to produce tissue closer to in vivo tissue. A vascular network structure may be formed only in the cell structure, or may be formed so that at least part of the vascular network structure is exposed to the surface or bottom of the cell structure.

The endothelial cells contained in the cell structure according to the present embodiment may be vascular endothelial cells or lymphatic endothelial cells. Moreover, both vascular endothelial cells and lymphatic endothelial cells may be contained.

There is no particular limit on the cell species of the cells other than the endothelial cells included in the cell structure according to the present embodiment, as long as the cells of the cell species do not inhibit the endothelial cells from forming a vascular network. The cell species can be selected as appropriate in consideration to the kind of the body fluid specimen and the in vivo environment. The cells other than the endothelial cells in the cell structure according to the present embodiment are preferably cells that constitute surrounding tissue of vessels in a living body, because the endothelial cells can easily form a vessel network maintaining the original function and shape. Examples of these cells include fibroblasts, neural cells, dendritic cells, macrophages, and mast cells, epithelial cells, cardiac cells, liver cells, pancreatic islet cells, tissue stem cells, smooth muscle cells, and others. Moreover, the cell structure may contain, other than endothelial cells, one type of cell, or two or more types of cells. In the cell structure according to the present embodiment, the cells other than the endothelial cells are preferably cells including at least fibroblasts, more preferably cells including vascular endothelial cells and fibroblasts, cells including lymphatic endothelial cells and fibroblasts, or cells including vascular endothelial cells, lymphatic endothelial cells, and fibroblasts. The cells other than endothelial cells contained in the cell structure may be derived from the same organism species as that of the endothelial cells, or from different organism species.

The number of endothelial cells in the cell structure according to the present embodiment is not limited, as long as the number of endothelial cells is sufficient for forming a vascular network structure. The number of endothelial cells can be suitably determined in consideration of the size of the cell structure, the type of endothelial cells, the type of cells other than endothelial cells, etc. For example, a cell structure in which a vascular network structure is formed can be prepared by setting the abundance ratio (cell number ratio) of endothelial cells to all the cells that constitute the cell structure according to the present embodiment to 0.1% or more. When fibroblasts are used as the cells other than endothelial cells, the number of endothelial cells in the cell structure according to the present embodiment is preferably 0.1% or more, more preferably in the range of 0.1 to 10.0%, and even more preferably in the range of 0.1 to 5.0%, of the number of fibroblasts. When both vascular endothelial cells and lymphatic endothelial cells are contained as endothelial cells, the total number of vascular endothelial cells and lymphatic endothelial cells is preferably 0.1% or more, preferably in the range of 0.1 to 10.0%, and even more preferably in the range of 0.1 to 5.0%, of the number of fibroblasts.

The type of cells which constitute the cell structure according to the present embodiment is not limited. The cells may be cells obtained from an animal, cells obtained by culturing cells obtained from an animal, cells obtained by subjecting cells obtained from an animal to various treatments, or cultured cell lines. In the case of cells obtained from an animal, the sampling site is not limited. The cells may be somatic cells derived from the bone, muscle, viscus, nerve, brain, bone, skin, blood, etc.; reproductive cells; or embryonic stem cells (ES cells). Moreover, the organism species from which the cells constituting the cell structure according to the present embodiment are derived is not limited. For example, usable cells can be derived from humans, or animals such as monkeys, dogs, cats, rabbits, pigs, cows, mice, and rats. The cells obtained by culturing cells obtained from an animal may be primary cultured cells or subcultured cells. The cells obtained by applying various treatments may include induced pluripotent stem cells (iPS cells) or cells after differentiation induction. The cell structure according to the present embodiment may be composed of only cells derived from the same organism species, or cells derived from several types of organism species.

The cells constituting the cell structure according to the present embodiment are all normal cells. In general, the normal cells are non-cancerated cells that have the ability to grow or stop growth depending on the body and surrounding circumferences.

The normal cells constituting the cell structure according to the present embodiment may be cells taken from animals not having cancer, cells (cell lines) that are separated from animals not having cancer, and are immortalized and maintained stably in vitro, or non-cancerated cells that are separated from animals not having cancer and are genetically modified in an artificial way. Otherwise, the normal cells constituting the cell structure may be non-cancerated cultured cell lines.

There are no particular limits on the size and shape of the cell structure according to the present embodiment as long as it can form a vascular network structure. Because it is possible to form a vascular network structure in a state closer to vessels formed in in vivo tissue, the thickness of the cell structure is preferably 5 μm or more, more preferably 10 μm or more, even more preferably 50 μm or more, and still more preferably 100 μm or more. The thickness of the cell structure is preferably 500 μm or less, more preferably 400 μm or less, and even more preferably 300 μm or less. The number of cell layers in the cell structure according to the present embodiment is preferably approximately in the range of 2 to 60, more preferably approximately in the range of 5 to 60, further preferably approximately in the range of 10 to 60.

The number of cell layers that constitute the cell structure is measured by dividing the total number of cells that constitute a three-dimensional structure by the number of cells per layer (the number of cells necessary to form one layer). The number of cells per layer can be examined in such a manner that cells are previously cultured on a plane so that they are confluent in a cell culture vessel that is used in the production of a cell structure. Specifically, the number of cell layers in a cell structure formed in a certain cell culture vessel can be calculated by counting the total number of cells that constitute the cell structure, and dividing the total number of cells by the number of cells per layer in the cell culture vessel.

In general, the cell structure according to the present embodiment is produced in a cell culture vessel. The cell culture vessel is not limited, as long as it enables the production of a cell structure and enables the culture of the produced cell structure. Specific examples of the cell culture vessel include dishes, cell culture inserts (e.g., Transwell (registered trademark) inserts, Netwell (registered trademark) inserts, Falcon (registered trademark) cell culture inserts, and Millicell (registered trademark) cell culture inserts), tubes, flasks, bottles, plates, and the like. In the production of the cell structure according to the present embodiment, dishes or various cell culture inserts are preferable, because they can more appropriately perform the prediction of cancerization using the cell structure.

The cell structure according to the present embodiment is at least a structure formed from multiple layers of cells with a vascular network structure, and there is no particular limit on the method of producing the cell structure. For example, the method may be a production method including sequentially laminating each layer, a method including forming two or more cell layers at once, or a method including forming multiple cell layers by suitably combining both production methods. Moreover, the cell structure according to the present embodiment may be a multilayer structure in which the type of cell that constitutes each layer is different for each layer, or the type of cell that constitutes each layer is the same in the all layers of the structure. For example, the method used may be a production method in which a layer is formed for every type of cell, the resulting cell layers are sequentially laminated, or a method in which a cell mixed solution containing a mixture of several types of cells is previously prepared, and a multilayer cell structure is produced at once from the cell mixed solution.

An example of the method of producing the cell structure by laminating each layer in sequence includes the method disclosed in JP 4919464 B, that is, repeating alternately a step of forming a cell layer and a step of bringing the formed cell layer into contact with a solution containing an extracellular matrix (ECM) component to laminate the cell layers in a continuous manner. For example, when this method is performed, a cell mixture containing all cells that constitute a cell structure is previously prepared, and each cell layer is formed from this cell mixture, thereby producing a cell structure in which a vascular network structure is formed in the entire structure. Further, cell layers may be formed for each cell type, thereby producing a cell structure in which a vascular network structure is formed only in a layer formed from endothelial cells.

As the method of forming two or more cell layers at once, for example, the method disclosed in JP 5850419 B can be used. Specifically, this method produces a cell structure having multiple cell layers by previously coating the entire cell surface with a polymer containing an arginine-glycine-aspartic acid (RGD) sequence bound to integrin, and a polymer interacting with the polymer containing the RGD sequence, accommodating the coated cells coated with an adhesive film in a cell culture vessel, and then integrating the coated cells by centrifugation or the like. For example, when this method is performed, it is possible to use coated cells prepared by previously preparing a cell mixture containing all cells that constitute a cell structure, and adding an adhesive component to the cell mixture. This enables the production of a cell structure in which a vascular network structure is formed in the entire structure by one centrifugation. Moreover, it is also possible to, for example, separately prepare coated cells coating endothelial cells, and coated cells coating fibroblasts, form a multilayer composed of the coated cells of fibroblasts, then laminate one layer formed from the coated cells of endothelial cells thereon, and further laminate a multilayer formed from the coated cells of fibroblasts thereon. This enables the production of a cell structure having a vascular network structure inserted between thick fibroblast layers.

The cell structure according to the present embodiment may also be produced by a method including the following steps (a) to (c):
(a) a step of mixing cells and an extracellular matrix component in a cationic buffer solution to obtain a mixture.
(b) a step of seeding the mixture obtained in step (a) in a cell culture vessel.
(c) a step of removing a liquid component from the cell mixture in the cell culture vessel after step (b), and obtaining a cell structure in which the cells are laminated in multiple layers in the cell culture vessel.

In the present embodiment, in step (a), cells are mixed with an extracellular matrix component and a buffer containing a cationic substance, (cationic buffer solution) and cell aggregates are formed from the cell mixture, thereby obtaining a three-dimensional cell tissue with few large voids therein. Because the obtained three-dimensional cell tissue is relatively stable, the cell tissue can be cultured at least for several days, and the tissue is hardly broken down during medium replacement.

Further, in the present embodiment, step (b) can also include precipitating, in a cell culture vessel, the cell mixture seeded in the cell culture vessel. The cell mixture may be actively precipitated by centrifugal separation or the like, or may be spontaneously precipitated.

In step (a), it is preferable to further mix the cells with a strong electrolyte polymer. When the cells are mixed with a cationic substance, a strong electrolyte polymer, and an extracellular matrix component, a thick three-dimensional cell tissue with few voids can be obtained even when the cells are spontaneously precipitated, without requiring treatment, such as centrifugal separation, for actively gathering the cells in step (b).

Examples of the cationic buffer solution include tris-hydrochloric acid buffers, tris-maleic acid buffers, bis-tris buffers, HEPES, and the like. There are no particular limits on the concentration and pH of the cationic substance in the cationic buffer solution (e.g., tris in the tris-hydrochloric acid buffer solution) unless it has an adverse effect on the growth of the cells and the production of the cell structure. For example, the concentration of the cationic substance in the cationic buffer solution can be in the range of 10 to 100 mM, preferably in the range of 40 to 70 mM, more preferably 50 mM. The pH of the cationic buffer solution can be in the range of 6.0 to 8.0, preferably in the range of 6.8 to 7.8, more preferably in the range of 7.2 to 7.6.

Examples of the strong electrolyte polymer include, but are not limited to, glycosaminoglycans, such as heparin, chondroitin sulfate (e.g., chondroitin 4-sulfate and chondroitin 6-sulfate), heparan sulfate, dermatan sulfate, keratan sulfate, and hyaluronic acid; dextran sulfate, rhamnan sulfate, fucoidan, carrageenan, polystyrene sulfonic acid, polyacrylamide-2-methylpropane sulfonic acid, polyacrylic acid, and derivatives thereof. The mixture prepared in step (a) may be mixed with only one strong electrolyte polymer, or two or more strong electrolyte polymers in combination. In the production of the cell structure according to the present embodiment, the polymer electrolyte is preferably glycosaminoglycan. In addition, using at least one of heparin, dextran sulfate, chondroitin sulfate, and dermatan sulfate is more preferred. The strong electrolyte polymer for use in the present embodiment is further preferably heparin.

The amount of strong electrolyte polymer mixed in the cationic buffer solution is not limited, as long as it does not adversely affect the cell growth and the production of the cell structure. For example, the concentration of the strong electrolyte polymer in the cationic buffer solution is more than 0 mg/mL and less than 1.0 mg/mL, preferably in the range of 0.025 to 0.1 mg/mL, and more preferably in the range of 0.05 to 0.1 mg/mL. Moreover, in the present embodiment, a cell structure can be produced by preparing the above mixture without mixing a strong electrolyte mentioned above.

Examples of the extracellular matrix component include collagen, laminin, fibronectin, vitronectin, elastin, tenascin, entactin, fibrillin, proteoglycan, modified forms or variants thereof, and the like. Examples of the proteoglycan include chondroitin sulfate proteoglycan, heparan sulfate proteoglycan, keratan sulfate proteoglycan, dermatan sulfate proteoglycan, and the like. The mixture prepared in step (a) may be mixed with only one extracellular matrix component, or two or more extracellular matrix components in combination. In the production of the cell structure according to the present embodiment, it is preferable to use collagen, laminin, or fibronectin; and it is particularly preferable to use collagen. Modified forms and variants of the extracellular matrix components mentioned above may also be used, as long as they do not adversely affect the cell growth and the formation of cell structure. The amount of extracellular matrix component mixed in the cationic buffer solution is not limited, as long as it does not adversely affect the cell growth and the production of the cell structure. For example, the concentration of the extracellular matrix component in the cationic buffer solution is more than 0 mg/mL and less than 1.0 mg/mL, preferably in the range of 0.025 to 0.1 mg/mL, and more preferably in the range of 0.05 to 0.1 mg/mL.

The mixing ratio of the strong electrolyte polymer to the extracellular matrix component mixed in the cationic buffer solution is in the range of 1:2 to 2:1. In the production of the cell structure according to the present embodiment, the mixing ratio of the strong electrolyte polymer to the extracellular matrix component is preferably in the range of 1:1.5 to 1.5:1, and more preferably 1:1.

A cell structure with sufficient thickness can be produced by repeating steps (a) to (c). Specifically, the following process is repeated: as step (b), the mixture prepared in step (a) is seeded on the cell structure obtained in a previous step (c), and step (c) is then performed. The cell composition of the mixture newly seeded in the cell structure obtained in step (c) may be the same as or different from the cell composition that constitute the already produced cell structure.

For example, first, a mixture containing only fibroblasts as cells is prepared in step (a), and steps (b) and (c) are performed to obtain a cell structure formed from 10 fibroblast layers in a cell culture vessel. Subsequently, as step (a), a mixture containing only vascular endothelial cells as cells is prepared, and steps (b) and (c) are performed to laminate one vascular endothelial cell layer on the 10 fibroblast layers in the cell culture vessel. Further, as step (a), a mixture containing only fibroblasts as cells is prepared, and steps (b) and (c) are performed to laminate 10 fibroblast layers on the vascular endothelial cell layer in the cell culture vessel. This enables the production of a cell structure in which 10 fibroblast layers, 1 vascular endothelial cell layer, and 10 fibroblast layers are sequentially laminated in layers for each cell type. The thickness of cell layers laminated in step (c) can be adjusted by controlling the number of cells seeded in step (b). The number of cell layers laminated in step (c) increases as a larger number of cells is seeded in step (b). Furthermore, a mixture containing all of the fibroblasts for 20 fibroblast layers, the vascular endothelial cells for 1 vascular endothelial cell layer, is prepared in step (a), then steps (b) and (c) are performed, thereby producing a cell structure having a thickness corresponding to the 21 layers, in which a vascular network structure is scattered in the structure.

When steps (a) to (c) are repeated, the obtained cell structure may be cultured after step (c) and before step (b). The conditions for the culture of the cell structure such as the composition of a culture medium for use in the culture, the culture temperature, the culture time, and the atmospheric composition at the time of culture are conditions suitable for the culture of the cells constituting the cell structure. Examples of the culture medium include D-MEM, E-MEM, MEMα, RPMI-1640, Ham's F-12, and the like.

After step (a), the following steps (a'-1) and (a'-2) may be performed, and then step (b) may be performed: (a'-1) a step of removing a liquid part from the obtained mixture, and obtaining cell aggregates, and (a'-2) a step of suspending the cell aggregates in a solution.

Moreover, after step (a), the following steps (b'-1) and (b'-2) may be performed in place of step (b). In the present embodiment and the present specification, the term "cell viscous body" refers to gel-like cell aggregates as disclosed in NPL 2.

(b'-1) a step of seeding the mixture obtained in step (a) in a cell culture vessel, and then removing a liquid component from the mixture to obtain a cell viscous body; and (b'-2) a step of suspending the cell viscous body in a solvent in the cell culture vessel. A desired tissue body can be obtained by carrying out the above steps (a) to (c); however, a more uniform tissue body can be obtained by carrying out steps (a'-1) and (a'-2) after step (a), and then carrying out step (b).

The solvent for preparing a cell suspension is not limited, as long as it does not have toxicity to the cells, and does not impair proliferative properties or function. Water, buffers, cell culture media, etc., can be used. Examples of the buffer include phosphate-buffered saline (PBS), HEPES, Hanks' buffers, and the like. Examples of culture media include D-MEM, E-MEM, MEMα, RPMI-1640, Ham's F-12, and the like.

The following step (c') may be performed in place of step (c).

(c') a step of removing a liquid component from the seeded mixture, and forming a cell layer on the substrate.

The method of removing the liquid component in steps (c) and (c') is not limited, as long as it does not adversely affect the cell growth and the production of the cell structure. The method of removing a liquid component from a suspension of the liquid component and a solid component can be suitably performed by a method known to a person skilled in the art. Examples of the method include centrifugal separation, magnetic separation, filtration, and the like. For example, when a cell culture insert is used as the cell culture vessel, the cell culture insert in which the mixture is seeded can be subjected to centrifugal separation at 10° C. at 400×g for 1 minute to thereby remove the liquid component.

<Culture Step>

The cell structure according to the present embodiment is cultured in the presence of a biological specimen derived from a subject. The subject in the present embodiment means a cancer patient or a cancer suspect. Specifically, the cell structure is cultured in a culture medium mixed with a biological specimen derived from the subject.

The amount of the biological specimen mixed into the culture medium can be experimentally decided in consideration of culture conditions such as the kind of the biological specimen, the kinds and numbers of cells constituting the cell structure, the kind of the culture medium, the culture temperature, and the culture time.

In the method according to the present embodiment, there is no particular limit on applicable kinds of cancer. Examples of the kinds of cancer include, but not limited to, breast cancer (e.g., invasive ductal carcinoma, ductal carcinoma in situ, and inflammatory breast cancer), prostate cancer (e.g., hormone-dependent prostate cancer and hormone-independent prostate cancer), pancreatic cancer (e.g., pancreatic duct cancer), gastric cancer (e.g., papillary adenocarcinoma, mucinous adenocarcinoma, and adenosquamous carcinoma), lung cancer (e.g., non-small-cell lung cancer, small-cell lung cancer, and malignant mesothelioma), colon cancer (e.g., gastrointestinal stromal tumor), rectal cancer (e.g., gastrointestinal stromal tumor), colorectal cancer (e.g., familial colorectal cancer, hereditary nonpolyposis colorectal cancer, and gastrointestinal stromal tumor), small intestinal cancer (e.g., non-Hodgkin's lymphoma and gastrointestinal stromal tumor), esophageal cancer, duodenal cancer, tongue cancer, pharyngeal cancer (e.g., nasopharyngeal cancer, oropharynx cancer, and hypopharyngeal cancer), head and neck cancer, salivary gland cancer, brain tumor (e.g., pineal astrocytoma, pilocytic astrocytoma, diffuse astrocytoma, and anaplastic astrocytoma), neurilemmoma, liver cancer (e.g., primary liver cancer and extrahepatic bile duct cancer), renal cancer (e.g., renal cell cancer and transitional cell cancer of the renal pelvis and ureter), gallbladder cancer, bile duct cancer, pancreatic cancer, hepatoma, endometrial cancer, cervical cancer, ovarian cancer (e.g., epithelial ovarian cancer, extragonadal germ cell tumor, ovarian germ cell tumor, and ovarian low-malignant potential tumor), bladder cancer, urethral cancer, skin cancer (e.g., intraocular (ocular) melanoma and Merkel cell carcinoma), hemangioma, malignant lymphoma (e.g., reticulosarcoma, lymphosarcoma, and Hodgkin's disease), melanoma (malignant melanoma), thyroid cancer (e.g., medullary thyroid cancer), parathyroid cancer, nasal cancer, paranasal cancer, bone tumor (e.g., osteosarcoma, Ewing's tumor, uterine sarcoma, and soft-tissue sarcoma), metastatic medulloblastoma, hemangiofibroma, dermatofibrosarcoma protuberans, retinal sarcoma, penile cancer, testicular tumor, pediatric solid cancer (e.g., Wilms tumor and pediatric renal tumor), Kaposi sarcoma, Kaposi sarcoma caused by AIDS, tumor of maxillary sinus, fibrous histiocytoma, leiomyosarcoma, rhabdomyosarcoma, chronic myeloproliferative disorders, leukemia (e.g., acute myelogenous leukemia and acute lymphoblastic leukemia), and the like.

Examples of the biological specimen derived from the subject for use in the present embodiment include a body fluid specimen taken from the subject, a cell extract of cells taken from the subject, and a culture supernatant of cells taken from the subject. The cell extract and the culture supernatant both contain exosomes secreted from the cells and thus can be used as well as the body fluid specimen taken from the subject.

There is no particular limit on the body fluid specimen taken from the subject for use in the present embodiment as long as it is derived from cancer cells and contains nucleic acids and proteins involved in cancerization. In the present embodiment, the body fluid specimen preferably contains exosomes. Exosomes are contained in most of body fluids. Accordingly, there is no particular limit on the body fluid specimen taken from the subject for use in the present embodiment. Body fluids generally taken in liquid biopsy can be used such as blood, blood serum, blood plasma, urine, buffy coat, saliva, semen, chest exudate, cerebrospinal fluid, tear fluid, phlegm, mucus, lymph, ascites, pleural effusion, amniotic fluid, bladder lavage fluid, and bronchoalveolar lavage fluid.

In the culture step, the body fluid to be added to the culture medium with the cell structure may be a body fluid taken directly from the subject or a specimen pre-processed by diluting the taken body fluid with a buffer solution or extracting a specific component from the taken body fluid. For example, exosomes may be collected, concentrated, refined, or isolated from the body fluid specimen. The method of collection, concentration, refinement, or isolation can be arbitrarily selected depending on the kind of the body fluid specimen listed above and its state.

The culture medium for use in the culture step can be selected as appropriate depending on the kind of the cells as long as it provides a basic medium containing components necessary for the survival growth of the cells (inorganic salts, carbohydrates, hormones, essential amino acids, non-essential amino acids, and vitamins). Examples of the culture medium include, but not limited to, D-MEM, Minimum Essential Medium (MEM), RPMI-1640, Basal Medium Eagle (BME), Dulbecco's Modified Eagle's Medium: Nutrient Mixture F-12 (D-MEM/F-12), Glasgow Minimum Essential Medium (Glasgow MEM), and others.

In the culture step, the culture temperature is preferably in the range of 25° C. or more and 40° C. or less, more preferably in the range of 30° C. or more and 39° C. or less, further preferably in the range of 35° C. or more and 39° C. or less. The culture environment can be arbitrarily set as long as it has no direct influence on the maintenance of medicines, cells, and tissue and it lasts in a manner suitable for the culture of the cells for an arbitrary period of time. Further, hydrodynamic loads, such as reflux, may be applied, if necessary, within a range that does not greatly change the culture environment. The culture environment may be a $CO_2$ condition of about 5%, for example.

In the culture step, the culture period can be arbitrarily set depending on the origin and amount of the liquid substance. The culture period is preferably in the range of 3 days or more and 14 days or less, more preferably in the range of 4 days or more and 10 days or less, further preferably in the range of 4 days or more and 8 days or less.

In the culture step, the number of the exosomes may be arbitrarily set depending on the kind and number of the normal cells. The number of the exosomes is preferably, for example, $1 \times 10^3$ or more relative to the normal cells of $2 \times 10^6$, more preferably $1 \times 10^7$ or more, and further preferably in the range of $1 \times 10^7$ or more and $1 \times 10^{12}$ or less.

<Assessment Step>

Subsequently, the possibility of cancerization in the subject is assessed using the state of the vessels in the cell structure after the culture as an index. Specifically, when the number of the cells constituting the vessels in the cell structure is large or the vascular network structure in the cell structure is extended as compared to the case of culturing the cells in the absence of a biological specimen, it is assessed that the possibility of cancerization is high in the subject. On the other hand, when the number of the cells constituting the vessels in the cell structure is small or the vascular network structure in the cell structure is not extended as compared to the case of culturing the cells in the absence of a biological specimen, it is assessed that the possibility of cancerization is low in the subject.

The presence or absence of extension of the vessels can be determined, for example, by labeling the cells constituting the vessels to discriminate them from the other cells and using a signal from the label as an index. For example, fluorescently labeling the cells constituting the vessels allows direct observation of the vessels in the cell structure. In addition, some image analysis technique can be used to compare a fluorescent image of the cell structure cultured in the presence of a biological specimen to a fluorescent image of the cell structure cultured in the absence of a biological specimen to determine whether the extension of the vascular network structure is accelerated by the biological specimen. The fluorescent labeling of the cells constituting the vessels can be performed by a known method, such as immunostaining, which uses, for example, an antibody against a substance specifically expressed on the cell surface of cells constituting the vessels as a primary antibody, and a fluorescently-labeled secondary antibody capable of specifically binding to the primary antibody.

Similarly, the number of the cells constituting the vessels can be determined by labeling the cells constituting the vessels (endothelial cells) and using a signal from the label as an index. For example, in the case of fluorescently labeling the cells constituting the vessels, the total fluorescence intensity or the area of fluorescence emission region of a fluorescence image of the cell structure depends on the number of cells constituting the vessels. When the number of the cells constituting the vessels is large, the total fluorescence intensity becomes high and the area of the florescence emission region becomes large. Accordingly, comparing a fluorescent image of the cell structure cultured in the presence of a biological specimen and a fluorescent image of the cell structure cultured in the absence of a biological specimen for the fluorescence intensity or the area of the fluorescence emission region allows comparison of the number of the cells constituting the vessels. Alternatively, the three-dimensional conformation of the cell structure after labeling the cells constituting the vessels may be destroyed so that only the number of the labeled cells can be directly counted by fluorescence activated cell sorting (FACS) or the like.

Examples of the labeling substance for labeling the endothelial cells include, but are not limited to, a fluorescent pigment, fluorescent beads, quantum dots, biotin, antibody, antigen, energy absorbing material, radioisotopes, chemical illumination, enzymes, and others. Among them, using a fluorescent pigment is preferred. Specific examples of the fluorescent pigment include carboxyfluorescein (FAM), 6-carboxy-4',5'-dichloro-2',7'-dimethoxy fluorescein (JOE), fluorescein isothiocyanate (FITC), tetrachloro-fluorescein (TET), 5'-hexachloro-fluorescein-CE phosphoramidite (HEX), Cy3, Cy5, Alexa568, Alexa647, PKH26, PKH67GL, and others.

《Kit for Assessing the Possibility of Cancerization》

A kit for assessing the possibility of cancerization in the subject according to an embodiment of the present invention includes a cell culture vessel and a cell structure that is formed from normal cells formed on the cell culture vessel and has a vascular network structure.

The kit according to the present embodiment makes it possible to assess the possibility of cancerization in the subject in a faster and simpler manner.

In the present embodiment, the cell culture vessel and the cell structure may be similar to the cell structure exemplified in 《Method of assessing the possibility of cancerization in the subject》 described above.

The kit according to the present embodiment may further include a culture medium for the cell structure, a labeling substance for labeling the vessel cells formed from endothelial cells, substances for use in production the cell structure (e.g., a cationic buffer solution, a strong electrolyte polymer, an extracellular matrix component, and others), a detection device for counting the number of cells in the cell structure, and others.

The culture medium may be similar to the culture medium exemplified in 《Method of assessing the possibility of cancerization in the subject》 described above. Examples of the detection device include a micro plate reader, a fluorescence scanner, a two-photon excitation scanner, a fluorescence microscope, and others.

EXAMPLES

The present invention will be described by means of examples. However, the present invention is not limited to those examples.

<Example 1> Assessment of Cancerization with Exosomes Derived from a Colorectal Cancer Cell Line (1)

For cells constituting a vascular network-structure-forming body formed from normal cells, two kinds of cells, that is, normal human dermal fibroblasts (NHDF) (CC-2509 produced by Lonza) and human umbilical vein endothelial cells (HUVEC) (CC-2517A produced by Lonza) were used. For a cell culture vessel, a Transwell cell culture insert (#3470 produced by Corning Inc.) was used. For a medium, D-MEM (043-30085 produced by Wako Pure Chemical Corp.) containing 10 vol/vol % bovine serum (EXO-FBS-50A-1 produced by System Biosciences Inc.) and 1 vol/vol % penicillin/streptomycin (168-23191 produced by Wako Pure Chemical Corp.) was used.

As the assessment method, vascular network formation was assessed by a combination of fluorescent labeling by an anti-CD31 antibody (JC70A M082329 produced by DAKO) and a secondary antibody (A-11001 produced by Invitrogen) and image analysis through direct observation.

For exosomes, exosomes collected by ultracentrifugation from a culture supernatant of a human colorectal adenocarcinoma cell line HCT116 (ATCC (registered trademark) CCL-247) were used for the assessment under four conditions that the number of the exosomes were 0, $1\times10^7$, $1\times10^8$, and $1\times10^9$.

As the image analysis method, the areas of fluorescent emission regions were measured by a box-type microscope (BZ-X700) produced by Keyence Corp.

The detailed procedure is as described below.

<1> Production of a Vascular Network-Structure-Forming Body Formed from Normal Cells (1) $2\times10^6$ NHDF and $3\times10^4$ HUVEC were suspended in a tris-hydrochloric acid buffer solution containing heparin and collagen (0.1 mg/mL heparin, 0.1 mg/mL collagen, and 50 mM tris; pH: 7.4) (step (a)).

(2) The cell suspensions were each centrifuged at room temperature at 400×g for 1 minute, the supernatant was removed (step (a'-1)), and then each cell suspension was resuspended in a suitable amount of medium (step (a'-2)).

(3) This cell suspension was seeded in the Transwell cell culture insert (step (b)) and subjected to 400×g centrifugation at ambient temperature for 1 minute to remove the liquid component.

(4) An appropriate amount of medium was added to the Transwell cell culture insert and then the cells were cultured for 24 hours in a $CO_2$ incubator (at 37° C. and with 5% $CO_2$) (step (c)).

<2> Addition and Coculture of the Exosomes (1) Appropriate amounts of medium and exosomes were mixed to prepare solutions respectively containing 0, $1\times10^7$, $1\times10^8$, and $1\times10^9$ exosomes.

(2) The exosome solutions were added to the Transwell cell culture insert and were cultured for in the range of 96 to 192 hours in a $CO_2$ incubator (at 37° C. and with 5% $CO_2$).

<3> Assessment of Vascular Network Formation

The areas of the fluorescence emission regions were measured by a combination of fluorescence labeling with an anti-CD31 antibody (JC70A M082329 produced by DAKO) and a secondary antibody (A-11001 produced by Invitrogen) and image analysis through direct observation. FIG. 1 and Table 1 show the measurement results.

TABLE 1

| | Number of added exosomes (pieces) | | | |
|---|---|---|---|---|
| | 0 | $10^7$ | $10^8$ | $10^9$ |
| Area of vascular network-derived fluorescence emission region ($\times 10^5$ µm$^2$) | 190 | 211 | 298 | 322 |
| Area of exosome-derived fluorescence emission region ($\times 10^4$ µm$^2$) | 0 | 13 | 327 | 1829 |

It has been found from FIG. 1 and Table 1 that vascular network formation was promoted, that is, cancerization was caused in the cases where the numbers of added exosomes were $1\times10^7$, $1\times10^8$, and $1\times10^9$ with predominance over the case where the number of added exosomes was 0. It has also been revealed that the florescence emission region was $190\times10$ µm$^2$ with 0 exosome, whereas the florescence emission region was $211\times10^5$ µm$^2$ with the $1\times10^7$ exosomes, $298\times10^5$ µm$^2$ with the $1\times10^8$ exosomes, and $311\times10^5$ µm$^2$ with the $1\times10^9$ exosomes, which demonstrates that vascular network formation was promoted that is, cancerization progressed, in proportion to the number of added exosomes.

Figure 2B:
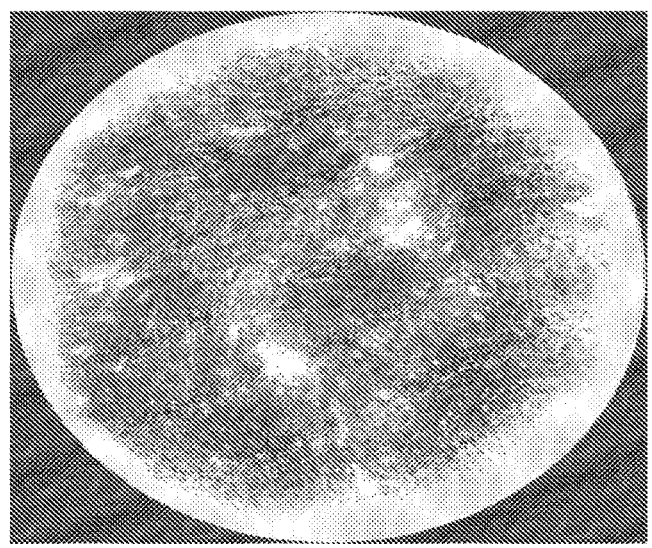
FIG. 2B is an image of the vascular network-derived fluorescent emission region and the exosome-derived fluorescent emission region in the cell structure in which the number of added exosomes is $1 \times 10^9$ in Example 1.
Figure 2A:
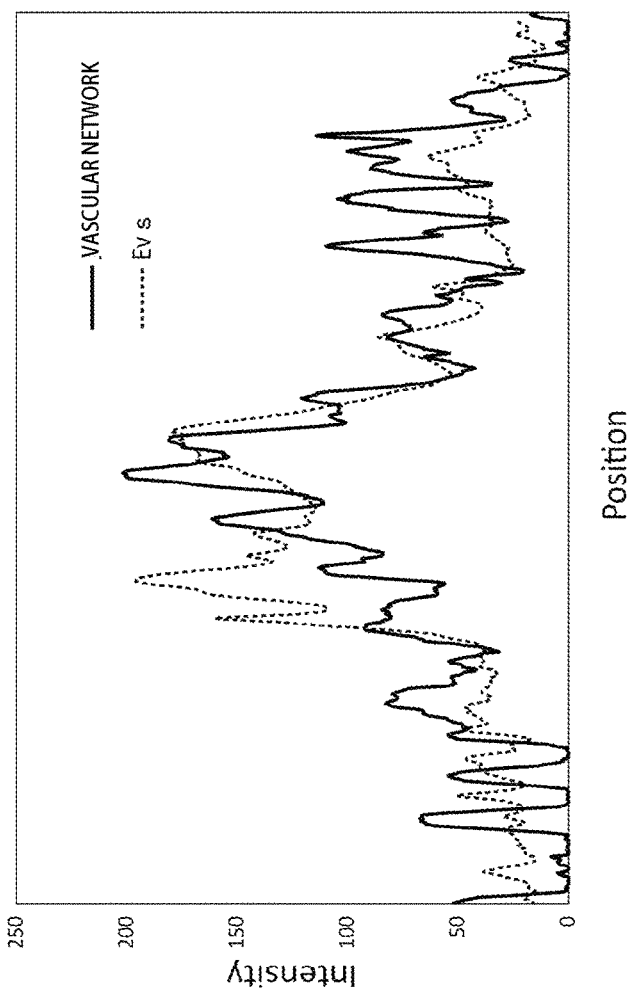
FIG. 2A is a graph indicating a fluorescent intensity profile of a fluorescent emission region shown in FIG. 2B in a cell structure in which the number of added exosomes is $1 \times 10^9$ in Example 1.

FIG. 2A shows the fluorescence intensity profile of the part of the cell structure with the $1\times10^9$ exosomes. In the drawing, the solid line indicates the intensity of fluorescence derived from the cells constituting the vascular network, and the dotted line indicates the intensity of fluorescence derived from the exosomes. In the positions where the intensity of fluorescence derived from the exosomes was high, the intensity of fluorescence derived from the cells constituting the vascular network was also relatively high, whereby it has been found that the vascular network formation was promoted by exosomes.

<Example 2> Assessment of Cancerization with Exosomes Derived from a Colorectal Cancer Cell Line (2)

Cell structures were produced in the same manner as in Example 1 except that the ratio of the number of HUVECs to the number of NHDFs (HUVEC content) was changed to 0.05, 0.25, 0.5, or 1.5%. As a result, a vascular network structure was formed in the cell structure provided with a HUVEC content of 0.25, 0.5, or 1.5%, whereas no vascular network structure was formed in the cell structure provided with a HUVEC content of 0.05%.

The cell structure body was cultured in the presence of exosomes in the same manner as in Example 1 except that the number of added exosomes was 0 or $1\times10^8$ to assess for vascular network formation. Table 2 shows the assessment results.

TABLE 2

| | HUVEC/NHDF × 100 (%) | | | | |
|---|---|---|---|---|---|
| | 0.05 | 0.25 | 0.5 | 1.0 | 1.5 |
| Area of exosome-derived fluorescence emission region (EVs) ($\times 10^5$ µm$^2$) | 0 / $10^8$ | 0 / 0 | 56 / 94 | 88 / 198 | 135 / 272 | 190 / 298 |
| $10^8$ EVs/0 EV | — | 1.7 | 2.3 | 2.0 | 1.6 |

It has been found from Table 2 that, under all the conditions that the ratio of the number of HUVECs to the number of NHDFs was 0.05, 0.25, 0.5, 1.0, and 1.5%, vascular network formation was promoted, that is, cancerization was caused with the $1\times10^8$ exosomes as compared to the case with 0 exosome.

<Example 3> Assessment of Cancerization with Exosomes Derived from a Colorectal Cancer Cell Line (3)

A cell structure body was cultured in the presence of exosomes in the same manner as in Example 1 except that the number of added exosomes was 0 or $1\times10^8$ and the number of culture days were 4, 6, and 8 to assess for vascular network formation. Table 3 shows the assessment results.

TABLE 3

| | Number of culture days (days) | | |
|---|---|---|---|
| | 4 | 6 | 8 |
| Area of exosome-derived fluorescence emission region (EVs) (×10⁵ μm²)  0  $10^8$ | 98  155 | 152  246 | 190  322 |
| $10^8$ EV$_s$/0 EV | 1.6 | 1.6 | 1.7 |

It has been found from Table 3 that, under all the conditions that the numbers of the culture days were 4, 6, and 8, vascular network formation was promoted, that is, cancerization was caused with the 1×10⁸ exosomes as compared to the case with 0 exosome.

[Example 4] Assessment of Cancerization with a Cell Structure Formed from Lung-Derived Interstitial Cells In Example 4, instead of the cell structure formed from NHDFs and HUVECs in Examples 1 to 3 described above, a cell structure formed from lung-derived interstitial cells was examined.

For cells constituting a vascular network-structure-forming body formed from normal cells, two kinds of cells, that is, normal human pulmonary fibroblasts (NHPF) (product number: C-12360 produced by PromoCell GmbH) and human dermal microvascular endothelial cells (HMVEC-L) (product number: CC-2527 produced by Lonza) were used. For a cell culture vessel, a Transwell cell culture insert (#3470 produced by Corning Inc.) was used. For a medium, D-MEM (043-30085 produced by Wako Pure Chemical Corp.) containing 10 vol/vol % bovine serum (EXO-FBS-50A-1 produced by System Biosciences Inc.) and 1 vol/vol % penicillin/streptomycin (168-23191 produced by Wako Pure Chemical Corp.) was used.

As the assessment method, vascular network formation was assessed by a combination of fluorescent labeling by an anti-CD31 antibody (JC70A M082329 produced by DAKO) and a secondary antibody (A-11001 produced by Invitrogen) and image analysis through direct observation.

For a serum, a stage IV colorectal cancer patient-derived serum V1 was used. Exosomes were collected from the stage IV colorectal cancer patient-derived serum V1 by ultracentrifugation and re-suspended in a medium of the same volume as the original serum. Assessment was conducted under 3 conditions that the respective amounts of the added serum and exosomes were 0 μL, 10 μL, and 50 μL.

As the image analysis method, the areas of fluorescent emission regions were measured by a box-type microscope (BZ-X700) produced by Keyence Corp.

The detailed procedure is as described below.
<1> Production of a Vascular Network-Structure-Forming Body Formed from Normal Cells
(1) 2×10⁶ NHPFs and 1×10⁵ HMVEC-Ls were suspended in a tris-hydrochloric acid buffer solution containing heparin and collagen (0.1 mg/mL heparin, 0.1 mg/mL collagen, 50 mM tris, and pH 7.4) (step (a)).
(2) The cell suspensions were each centrifuged at room temperature at 400×g for 1 minute, the supernatant was removed (step (a'-1)), and then each cell suspension was resuspended in a suitable amount of medium (step (a'-2)).
(3) This cell suspension was seeded in a Transwell cell culture insert (step (b)) and subjected to 400×g centrifugation at room temperature for 1 minute.
(4) An appropriate amount of medium was added to the Transwell cell culture insert and then the cells were cultured for 24 hours in a CO₂ incubator (at 37° C. and with 5% CO₂) (step (c)).
<2> Addition and Coculture of the Serum and Exosomes
(1) An appropriate amounts of medium was mixed with 0 μL, 10 μL, and 50 μL of serums to prepare media solutions containing serum. In addition, an appropriate amount of medium was mixed with 0 μL, 10 μL, and 50 μL of exosomes to prepare media solutions containing exosomes.
(2) The media solutions containing serum or exosomes were added to the Transwell cell culture insert and then the cells were cultured for 144 hours in a CO₂ incubator (37° C. and 5% CO₂).
<3> Assessment of Vascular Network Formation
The areas of the fluorescence emission regions were measured by a combination of fluorescence labeling with an anti-CD31 antibody (JC70A M082329 produced by DAKO) and a secondary antibody (A-11001 produced by Invitrogen) and image analysis through direct observation. Tables 4 and 5 show the measurement results.

TABLE 4

| | Amount of added serum (μL) | | |
|---|---|---|---|
| | 0 | 10 | 50 |
| Area of vascular network-derived fluorescence emission region (×10⁵ μm²) | 252 | 359 | 481 |

TABLE 5

| | Amount of added exosomes (μL) | | |
|---|---|---|---|
| | 0 | 10 | 50 |
| Area of vascular network-derived fluorescence emission region (×10⁵ μm²) | 252 | 351 | 438 |

It can be seen from Table 4 that vascular network formation was promoted in the cases where the amounts of the added serum were 10 μL and 50 μL with predominance over the case where the amount of the added serum was 0 μL. In addition, the area of the fluorescence emission region was 252×10⁵ μm² with 0 μL added serum, whereas the area of the fluorescence emission region was 359×10⁵ μm² with 10 μL added serum and 481×10⁵ μm² with 50 μL added serum, which demonstrates that vascular network formation was promoted in proportion to the amount of the added serum.

As shown in Table 5, vascular network formation was promoted in the cases where the amounts of added exosomes were 10 μL and 50 μL with predominance over the case where the amount of added exosomes was 0 μL. In addition, the area of the fluorescence emission region was 252×10⁵ μm² with 0 added exosome, whereas the area of the fluorescence emission region was 351×10⁵ μm² with 10 μL added exosomes and 438×10⁵ μm² with 50 μL added exosomes, which demonstrates that vascular network formation was promoted in proportion to the amount of the added exosomes.

It has been found that, in the case of using the cell structure formed from NHPFs and HMVEC-Ls as lung-derived interstitial cells instead of the cell structures formed from NHDFs and HUVECs as in Examples 1 to 3, vascular network formation was promoted, that is, cancerization was caused by adding the cancer patient-derived serum or the cancer patient-derived exosomes to the cell structure.

<Example 5> Assessment of the Possibility of Cancerization with Commercial Clinical Colorectal Cancer Patient-Derived Serums (Stages III/IV)

For cells constituting a vascular network-structure-forming body formed from normal cells, two kinds of cells, that is, normal human dermal fibroblasts (NHDF) (CC-2509 produced by Lonza) and human umbilical vein endothelial cells (HUVEC) (CC-2517A produced by Lonza) were used. For a cell culture vessel, a Transwell cell culture insert (#3470 produced by Corning Inc.) was used. For a medium, D-MEM (043-30085 produced by Wako Pure Chemical Corp.) containing 10 vol/vol % bovine serum (EXO-FBS-50A-1 produced by System Biosciences Inc.) and 1 vol/vol % penicillin/streptomycin (168-23191 produced by Wako Pure Chemical Corp.) was used.

As the assessment method, vascular network formation was assessed by a combination of fluorescent labeling by an anti-CD31 antibody (JC70A M082329 produced by DAKO) and a secondary antibody (A-11001 produced by Invitrogen) and image analysis through direct observation.

For serums, stage III colorectal cancer patient-derived serum 024301S (006-20000 produced by ProteoGenex, Inc.) and stage IV colorectal cancer patient-derived serum 024249S (006-20000 produced by ProteoGenex, Inc.) were used to make assessments under 3 conditions that the amounts of addition were 0 µL, 10 µL, and 50 µL.

As the image analysis method, the areas of fluorescent emission regions were measured by a box-type microscope (BZ-X700) produced by Keyence Corp.

The detailed procedure is as described below.

<1> Production of a Vascular Network-Structure-Forming Body Formed from Normal Cells (1) $2\times10^6$ NHDF and $3\times10^4$ HUVEC were suspended in a tris-hydrochloric acid buffer solution containing heparin and collagen (0.1 mg/mL heparin, 0.1 mg/mL collagen, and 50 mM tris; pH: 7.4) (step (a)).

(2) The cell suspensions were each centrifuged at room temperature at 400×g for 1 minute, the supernatant was removed (step (a'-1)), and then each cell suspension was resuspended in a suitable amount of medium (step (a'-2)).

(3) This cell suspension was seeded in a Transwell cell culture insert (step (b)) and subjected to 400×g centrifugation at ambient temperature for one minute.

(4) An appropriate amount of medium was added to the Transwell cell culture insert and then the cells were cultured for 24 hours in a $CO_2$ incubator (at 37° C. and with 5% $CO_2$) (step (c)).

<2> Addition and Coculture of the Serums (1) Appropriate amounts of medium and 0 µL, 10 µL, and 50 µL of serums were mixed to prepare media solutions containing serum.

(2) The media solutions containing serum were added to the Transwell cell culture insert and were cultured for 144 hours in a $CO_2$ incubator (at 37° C. and with 5% $CO_2$).

<3> Assessment of Vascular Network Formation

The areas of the fluorescence emission regions were measured by a combination of fluorescence labeling with an anti-CD31 antibody (JC70A M082329 produced by DAKO) and a secondary antibody (A-11001 produced by Invitrogen) and image analysis through direct observation. Tables 6 and 7 show the measurement results.

TABLE 6

| Stage III colorectal cancer | Amount of added serum (µL) | | |
|---|---|---|---|
| patient-derived serum 024301S | 0 | 10 | 50 |
| Area of vascular network-derived fluorescence emission region ($\times10^5$ µm$^2$) | 133 | 619 | 628 |

TABLE 7

| Stage IV colorectal cancer | Amount of added serum (µL) | | |
|---|---|---|---|
| patient-derived serum 024249S | 0 | 10 | 50 |
| Area of vascular network-derived fluorescence emission region ($\times10^5$ µm$^2$) | 133 | 310 | 269 |

It can be seen from Table 6 that vascular network formation was promoted in the cases where the amounts of the added stage III colorectal cancer patient-derived serum 024301S were 10 µL and 50 µL with predominance over the case where the amount of the added serum was 0 µL. In addition, the area of the fluorescence emission region was $133\times10^5$ µm$^2$ with 0 µL added serum, whereas the area of the fluorescence emission region was $619\times10^5$ µm$^2$ with 10 µL added serum and $628\times10^5$ µm$^2$ with 50 µL added serum, which demonstrates that vascular network formation was promoted in proportion to the amount of the added serum.

It can be seen from Table 7 that vascular network formation was promoted in the cases where the amounts of the added stage IV colorectal cancer patient-derived serum 24249S were 10 µL and 50 µL with predominance over the case where the amount of the added serum was 0 µL. In addition, the area of the fluorescence emission region was $133\times10^5$ µm$^2$ with 0 µL added serum, whereas the area of the fluorescence emission region was $310\times10^5$ µm$^2$ with 10 µL added serum and $269\times10^5$ µm$^2$ with 50 µL added serum.

These results have revealed that, according to the assessment method in the above embodiment of the present invention, colorectal cancer patients in at least stage III and subsequent stages can be determined.

<Example 6> Assessment of the Possibility of Cancerization with Commercial Clinical Lung Cancer Patient-Derived Serums (Stage IV)

For cells constituting a vascular network-structure-forming body formed from normal cells, two kinds of cells, that is, normal human dermal fibroblasts (NHDF) (CC-2509 produced by Lonza) and human umbilical vein endothelial cells (HUVEC) (CC-2517A produced by Lonza) were used. For a cell culture vessel, a Transwell cell culture insert (#3470 produced by Corning Inc.) was used. For a medium, D-MEM (043-30085 produced by Wako Pure Chemical Corp.) containing 10 vol/vol % bovine serum (EXO-FBS-50A-1 produced by System Biosciences Inc.) and 1 vol/vol % penicillin/streptomycin (168-23191 produced by Wako Pure Chemical Corp.) was used.

As the assessment method, vascular network formation was assessed by a combination of fluorescent labeling by an anti-CD31 antibody (JC70A M082329 produced by DAKO) and a secondary antibody (A-11001 produced by Invitrogen) and image analysis through direct observation.

For serums, stage IV lung cancer patient-derived serums 024427S and 024435S (006-20000 produced by ProteoGenex, Inc.) were used to make assessments under 2 conditions that the amounts of addition were 0 µL and 2 µL.

As the image analysis method, the areas of fluorescent emission regions were measured by a box-type microscope (BZ-X700) produced by Keyence Corp.

The detailed procedure is as described below.

<1> Production of a Vascular Network-Structure-Forming Body Formed from Normal Cells (1) $2 \times 10^6$ NHDF and $3 \times 10^4$ HUVEC were suspended in a tris-hydrochloric acid buffer solution containing heparin and collagen (0.1 mg/mL heparin, 0.1 mg/mL collagen, and 50 mM tris; pH: 7.4) (step (a)).

(2) The cell suspensions were each centrifuged at room temperature at 400×g for 1 minute, the supernatant was removed (step (a'-1)), and then each cell suspension was resuspended in a suitable amount of medium (step (a'-2)).

(3) This cell suspension was seeded in a Transwell cell culture insert (step (b)) and subjected to 400×g centrifugation at room temperature for 1 minute.

(4) An appropriate amount of medium was added to the Transwell cell culture insert and then the cells were cultured for 24 hours in a $CO_2$ incubator (at 37° C. and with 5% $CO_2$) (step (c)).

<2> Addition and Coculture of the Serums (1) An appropriate amount of medium and 0 μL and 2 μL of serums were mixed to prepare media solutions containing serum.

(2) The media solutions containing serum were added to the Transwell cell culture insert and were cultured for 144 hours in a $CO_2$ incubator (at 37° C. and with 5% $CO_2$).

<3> Assessment of Vascular Network Formation

The areas of the fluorescence emission regions were measured by a combination of fluorescence labeling with an anti-CD31 antibody (JC70A M082329 produced by DAKO) and a secondary antibody (A-11001 produced by Invitrogen) and image analysis through direct observation. Tables 8 and 9 show the measurement results.

TABLE 8

| Stage IV lung cancer | Amount of added serum (μL) | |
|---|---|---|
| patient-derived serum 024427S | 0 | 2 |
| Area of vascular network-derived fluorescence emission region (×$10^5$ μm$^2$) | 383 | 668 |

TABLE 9

| Stage IV lung cancer | Amount of added serum (μL) | |
|---|---|---|
| patient-derived serum 024435S | 0 | 2 |
| Area of vascular network-derived fluorescence emission region (×$10^5$ μm$^2$) | 383 | 533 |

It can be seen from Tables 8 and 9 that, with either of the stage IV lung cancer patient-derived serums, vascular network formation was promoted in the case where the amount of the added serum was 2 μL with predominance over the case where the amount of the added serum was 0 μL. In addition, the area of the fluorescence emission region was $383 \times 10^5$ μm$^2$ with 0 μL added serum, whereas the area of the fluorescence emission region was $668 \times 10^5$ μm$^2$ with 2 μL serum 024427S and $533 \times 10^5$ μm$^2$ with 2 μL serum 024435S, which demonstrates that vascular network formation was promoted with the addition of the serum.

These results have revealed that, according to the assessment method in the above embodiment of the present invention, lung cancer patients in at least stage IV can be determined.

<Example 7> Assessment of the Possibility of Cancerization with Clinical Colorectal Cancer Patient-Derived Serums (Stage IV)

Two kinds of cells, that is, normal human dermal fibroblasts (NHDF) (CC-2509 produced by Lonza) and GFP expression human umbilical vein endothelial cells (GFP-HUVEC) (cAP-0001GFP produced by Funakoshi Co., Ltd.) were used. For a cell culture vessel, a Transwell cell culture insert (#3470 produced by Corning Inc.) was used. For a medium, D-MEM (043-30085 produced by Wako Pure Chemical Corp.) containing 10 vol/vol % bovine serum (EXO-FBS-50A-1 produced by System Biosciences Inc.) and 1 vol/vol % penicillin/streptomycin (168-23191 produced by Wako Pure Chemical Corp.) was used.

As the assessment method, vascular network formation was assessed by a combination of GFP protein and image analysis through direct observation.

For serums, stage IV colorectal cancer patient-derived serums V1 and V2 actually obtained from clinical colorectal cancer patients (2 stage IV colorectal cancer patient-derived serum specimens actually obtained from clinical colorectal cancer patients) were used to make assessments under 3 conditions that the amounts of addition were 0 μL, 10 μL, and 50 μL. In addition, for reference, the case of using a healthy person-derived serum was assessed in the same manner.

As the image analysis method, the areas of fluorescent emission regions were measured by a box-type microscope (BZ-X700, BZ-9000) produced by Keyence Corp.

The detailed procedure is as described below.

<1> Production of a Vascular Network-Structure-Forming Body Formed from Normal Cells (1) $2 \times 10^6$ NHDFs and $3 \times 10^4$ GFP-HUVECs were suspended in a tris-hydrochloric acid buffer solution containing heparin and collagen (0.1 mg/mL heparin, 0.1 mg/mL collagen, 50 mM tris, and pH 7.4) (step (a)).

(2) The cell suspensions were each centrifuged at room temperature at 400×g for 1 minute, the supernatant was removed (step (a'-1)), and then each cell suspension was resuspended in a suitable amount of medium (step (a'-2)).

(3) This cell suspension was seeded in a Transwell cell culture insert (step (b)) and subjected to 400×g centrifugation at room temperature for 1 minute.

(4) An appropriate amount of medium was added to the Transwell cell culture insert and then the cells were cultured for 24 hours in a $CO_2$ incubator (at 37° C. and with 5% $CO_2$) (step (c)).

<2> Addition and Coculture of the Serums (1) Appropriate amounts of medium and 0 μL, 10 μL, and 50 μL of serums were mixed to prepare media solutions containing serum.

(2) The media solutions containing serum were added to the Transwell cell culture insert and were cultured for 144 hours in a $CO_2$ incubator (at 37° C. and with 5% $CO_2$).

<3> Assessment of Vascular Network Formation

The areas of the fluorescence emission regions were measured by a combination of GFP protein and image analysis through direct observation. Tables 10 to 12 show the measurement results.

TABLE 10

| Stage IV colorectal cancer | Amount of added serum (μL) | | |
|---|---|---|---|
| patient-derived serum V1 | 0 | 10 | 50 |
| Area of vascular network-derived fluorescence emission region ($\times 10^5$ μm$^2$) | 341 | 403 | 622 |

TABLE 11

| Stage IV colorectal cancer | Amount of added serum (μL) | | |
|---|---|---|---|
| patient-derived serum V2 | 0 | 10 | 50 |
| Area of vascular network-derived fluorescence emission region ($\times 10^5$ μm$^2$) | 341 | 773 | 705 |

TABLE 12

| | Amount of added serum (μL) | | |
|---|---|---|---|
| Healthy person-derived serum | 0 | 10 | 50 |
| Area of vascular network-derived fluorescence emission region ($\times 10^5$ μm$^2$) | 341 | 331 | 360 |

It can be seen from Tables 10 and 11 that, with either of the stage IV colorectal cancer patient-derived serums, vascular network formation was promoted in the cases where the amounts of the added serum were 10 μL and 50 μL with predominance over the case where the amount of the added serum was 0 μL. The area of the fluorescence emission region was 341×10$^5$ μm$^2$ with 0 μL added V1 serum, whereas the area of the fluorescence emission region was 403×10$^5$ μm$^2$ with 10 μL added V1 serum and 622×10$^5$ μm$^2$ with 50 μL added V1 serum as shown in Table 10. The area of the fluorescence emission region was 341×10$^5$ μm$^2$ with 0 μL added V2 serum, whereas the area of the fluorescence emission region was 773×10$^5$ μm$^2$ with 10 μL added V2 serum and 705×10$^5$ μm$^2$ with 50 μL added V2 as shown in Table 11. This demonstrates that vascular network formation was promoted in proportion to the amount of the added serum.

In contrast to this, as shown in Table 12, in either case of using 10 μL or 50 μL added healthy person-derived serum, vasculature formation was on almost the same level as in the case with 0 μL added healthy person-derived serum. In addition, the area of the fluorescence emission region was 341×10$^5$ μm$^2$ with 0 μL added healthy person-derived serum, whereas the area of the fluorescence emission region was 331×10$^5$ μm$^2$ with 10 μL added healthy person-derived serum and 360×10$^5$ μm$^2$ with 50 μL added healthy person-derived serum as shown in Table 12, which demonstrates that vascular network formation was on almost the same level regardless of the amount of the added serum.

It has been found that, according to the assessment method in the above embodiment of the present invention, the possibility of cancerization can also be determined by using serums actually obtained from clinical colorectal cancer patients.

<Example 8> Assessment of the Possibility of Cancerization with Clinical Colorectal Cancer Patient Serum-Derived Exosomes (Stage IV)

Two kinds of cells, that is, normal human dermal fibroblasts (NHDF) (CC-2509 produced by Lonza) and GFP expression human umbilical vein endothelial cells (GFP-HUVEC) (cAP-0001GFP produced by Funakoshi Co., Ltd.) were used. For a cell culture vessel, a Transwell cell culture insert (#3470 produced by Corning Inc.) was used. For a medium, D-MEM (043-30085 produced by Wako Pure Chemical Corp.) containing 10 vol/vol % bovine serum (EXO-FBS-50A-1 produced by System Biosciences Inc.) and 1 vol/vol % penicillin/streptomycin (168-23191 produced by Wako Pure Chemical Corp.) was used.

As the assessment method, vascular network formation was assessed by a combination of GFP protein and image analysis through direct observation.

For exosomes, exosomes collected by ultracentrifugation from the stage IV colorectal cancer patient-derived serum V1 actually obtained from a clinical colorectal cancer patient and re-suspended in the same volume of medium as the original serum amount were used to perform assessments under 3 conditions that the amounts of addition were 0 μL, 10 μL, and 50 μL. In addition, for reference, the same assessment was made with exosomes derived from a healthy person serum and a liquid component obtained by removing an exosome fraction from the stage IV colorectal cancer patient-derived serum V1 (hereinafter, also called serum supernatant).

As the image analysis method, the areas of fluorescent emission regions were measured by a box-type microscope (BZ-X700, BZ-9000) produced by Keyence Corp.

The detailed procedure is as described below.

<1> Production of a Vascular Network-Structure-Forming Body Formed from Normal Cells (1) 2×10$^6$ NHDFs and 3×10$^4$ GFP-HUVECs were suspended in a tris-hydrochloric acid buffer solution containing heparin and collagen (0.1 mg/mL heparin, 0.1 mg/mL collagen, 50 mM tris, and pH 7.4) (step (a)).

(2) The cell suspensions were each centrifuged at room temperature at 400×g for 1 minute, the supernatant was removed (step (a'-1)), and then each cell suspension was resuspended in a suitable amount of medium (step (a'-2)).

(3) This cell suspension was seeded in a Transwell cell culture insert (step (b)) and subjected to 400×g centrifugation at room temperature for 1 minute.

(4) An appropriate amount of medium was added to the Transwell cell culture insert and then the cells were cultured for 24 hours in a CO$_2$ incubator (at 37° C. and with 5% CO$_2$) (step (c)).

<2> Addition and Coculture of the Exosomes and Serum Supernatant (1) An appropriate amounts of medium was mixed with 0 μL, 10 μL, and 50 μL of exosomes suspensions to prepare media solutions containing exosomes. In addition, an appropriate amount of medium was mixed with 0 μL, 10 μL, and 50 μL of serum supernatant to prepare media solutions containing serum supernatant.

(2) The media solutions containing exosomes or serum supernatant were added to the Transwell cell culture insert and then the cells were cultured for 144 hours in a CO$_2$ incubator (37° C. and 5% CO$_2$).

<3> Assessment of Vascular Network Formation

The areas of the fluorescence emission regions were measured by a combination of GFP protein and image analysis through direct observation. Tables 13 to 15 show the measurement results.

TABLE 13

| Stage IV colorectal cancer patient serum | Amount of added exosomes (μL) | | |
|---|---|---|---|
| | 0 | 10 | 50 |
| V1-derived exosomes | | | |
| Area of vascular network-derived fluorescence emission region (×10⁵ μm²) | 344 | 423 | 617 |

TABLE 14

| Stage IV colorectal cancer patient serum | Amount of added serum supernatant (μL) | | |
|---|---|---|---|
| | 0 | 10 | 50 |
| V1-derived serum supernatant | | | |
| Area of vascular network-derived fluorescence emission region (×10⁵ μm²) | 344 | 354 | 387 |

TABLE 15

| | Amount of added exosomes (μL) | | |
|---|---|---|---|
| | 0 | 10 | 50 |
| Healthy person-derived exosomes | | | |
| Area of vascular network-derived fluorescence emission region (×10⁵ μm²) | 344 | 334 | 343 |

It can be seen from Table 13 that vascular network formation was promoted in the cases where the amounts of the added stage IV colorectal cancer patient serum V1-derived exosomes were 10 μL and 50 μL with predominance over the case where the amount of the added exosomes was 0 μL. In addition, the area of the fluorescence emission region was 344×10⁵ μm² with 0 μL added exosomes, whereas the area of the fluorescence emission region was 423×10⁵ μm² with 10 μL added exosomes and 617×10⁵ μm² with 50 μL added exosomes, which demonstrates that vascular network formation was promoted in proportion to the amount of the added exosomes.

In contrast to this, as shown in Table 14, vascular network formation was slightly more promoted in the cases where the amounts of the added stage IV colorectal cancer patient serum V1-derived serum supernatant were 10 μL and 50 μL than in the case where the amount of the added serum supernatant was 0 μL. The area of the fluorescence emission region was 344×10⁵ μm² with 0 μL added serum supernatant, whereas the area of the fluorescence emission region was 354×10⁵ μm² with 10 μL added serum supernatant and 387×10⁵ μm² with 50 μL added serum supernatant, which demonstrates that vascular network formation was slightly promoted in proportion to the amount of the added exosomes. However, in the case of adding the serum supernatant as a specimen obtaining by removing the exosomes through centrifugation, the effect of promoting vascular network formation is clearly smaller than that in the case of adding the exosomes.

In this way, a main advantageous effect of the above embodiment in the present invention such as vascular network formation was obtained by exosomes.

As shown in Table 15, in the case of using both 10 μL and 50 μL of the healthy human serum-derived exosomes, vascular network formation was on almost the same level as in the case where the added amount of the exosomes was 0 μL. The area of the fluorescence emission region was 344×10⁵ μm² with 0 μL added exosome, whereas the area of the fluorescence emission region was 334×10⁵ μm² with 10 μL added exosomes and 343×10⁵ μm² with 50 μL added exosomes as shown in Table 15, which demonstrates that vascular network formation was on almost the same level regardless of the amount of the added exosomes.

From these results, it is considered that exosomes are a component that has a main advantageous effect according to the above embodiment of the present invention such as vascular network formation.

It has been found that the possibility of cancerization can be determined by using exosomes in the assessment method according to the above embodiment of the present invention.

<Example 9> Production of Cell Structures with a Vasculature

Cell structures formed from fibroblasts and vascular endothelial cells and including a vascular network structure were produced and their vascular network structures were observed.

In Example 9, in the production of the cell structures with a vasculature, the ratio of the vascular endothelial cells to the fibroblasts enabling the formation of a cell structure with a vascular network structure was studied with changes in the amount of the vascular endothelial cells added to the fibroblasts.

For the cell structures with a vascular network structure, cell structures formed from two kinds of cells, that is, normal human dermal fibroblasts (NHDF) (CC-2509 produced by Lonza) and human umbilical vein endothelial cells (HUVEC) (CC-2517A produced by Lonza) were used. For a cell culture vessel, a Transwell cell culture insert (#3470 produced by Corning Inc.) was used. For a culture medium, D-MEM (043-30085 produced by Wako Pure Chemical Corp.) containing 10 vol/vol % bovine serum (EXO-FBS-50A-1 produced by System Biosciences Inc.) and 1 vol/vol % penicillin/streptomycin (168-23191 produced by Wako Pure Chemical Corp.) was used. For an angiogenesis inhibitor to be assessed, bevacizumab (product number: MAB293 produced by R&D Systems, Inc.) was used.

<Production of the Cell Structures>

First, 2×10⁶ NHDFs and HUVECs equivalent to 0.05, 0.1, 0.25, 0.5, 1.0, 1.5, 5.0% of the number of NHDFs were suspended in a tris-hydrochloric acid buffer solution containing heparin and collagen (0.1 mg/mL heparin, 0.1 mg/mL collagen, 50 mM tris, and pH 7.4) to prepare a cell suspension (the ratio of the number of HUVECs to the number of NHDFs was 5%) (step (a)). The cell suspension was subjected to 400×g centrifugation at ambient temperature for one minute to remove the supernatant (step (a'-1)), and the cells were suspended again in an appropriate amount of medium (step (a'-2)). Then, the cell suspension was seeded in the Transwell cell culture insert (step (b)) and subjected to 400×g centrifugation at room temperature for 1 minute. After that, an appropriate amount of medium was added to the Transwell cell culture insert and then the cells were cultured for 96 hours in a CO₂ incubator (at 37° C. and with 5% CO₂) (step (c)).

<Fluorescent Labeling and Assessment of the Cells Constituting the Blood Vessels>

The cell structures were subjected to fluorescent immunostaining using an anti-CD31 antibody (JC70A M082329 produced by DAKO) and a secondary antibody (A-11001 produced by Invitrogen) for green fluorescent labeling of the blood vessels in the structures. The fluorescent-labeled cell structures were directly observed to determine the presence or absence of formation of a vascular network. Table 16 shows the results.

TABLE 16

| HUVEC content (%) | Presence or absence of formation of vascular network. |
|---|---|
| 0.05 | absence |
| 0.1 | presence |
| 0.25 | presence |
| 0.5 | presence |
| 1.0 | presence |
| 1.5 | presence |
| 5.0 | presence |

It can be seen from Table 16 that the formation of a vascular network structure was observed with the content of HUVECs equivalent to 0.1% or more the number of NHDFs.

That is, the formation of a vascular network structure was observed under all the conditions in Table 16 except for the case in which HUVECs equivalent to 0.05% of the number of NHDFs were contained.

As discussed above, the present application addresses the following; in most of current techniques under study for application as diagnostic methods, the amounts of specific nucleic acids and proteins included in exosomes in body fluids are measured. However, there has not been reported any inspection and diagnosis technique or method focusing on actual actions and effects of exosomes in the body.

An aspect of the present invention is to provide a method of assessing the possibility of cancerization in a subject in a fast, easy, and less invasive manner.

The inventors of the present invention found that a biological specimen such as a body fluid taken from a cancer patient included a factor secreted by cancer cells and contributing to cancerization. The inventors of the present invention investigated the influence of a biological specimen derived from a cancer patient or a cancer suspect on a vascular network structure in a cell structure formed from normal cells to discover a method of assessing the possibility of cancerization in the patient.

A method of assessing the possibility of cancerization according to a first aspect of the present invention includes: a culture step of culturing a cell structure formed from normal cells and including a vascular network structure in the presence of a biological specimen derived from a subject; and an assessment step of assessing the possibility of cancerization in the subject using the state of vessels in the cell structure after the culture step as an index. The biological specimen is a body fluid specimen taken from the subject, a cell extract from cells taken from the subject, or a culture supernatant of cells taken from the subject. In the assessment step, when the number of cells constituting the vessels in the cell structure is larger than the number of cells cultured in the absence of the body fluid specimen, or when the vascular network structure in the cell structure extends, it is assessed that the possibility of cancerization is high in the subject.

The body fluid specimen may be blood, blood serum, blood plasma, urine, buffy coat, saliva, semen, chest exudate, pleural effusion, amniotic fluid, bladder lavage fluid, or bronchoalveolar lavage fluid.

The biological specimen may include exosomes.

The cell structure may include one or more cells selected from the group consisting of vascular endothelial cells and lymphatic endothelial cells.

The cell structure may further include one or more cells selected from the group consisting of fibroblasts, neural cells, dendritic cells, macrophages, and mast cells.

The cell structure may further include fibroblasts and the total number of the vascular endothelial cells and the lymphatic endothelial cells in the cell structure may be 0.1% or more of the number of cells of the fibroblasts.

The cell structure may have a thickness in the range of 5 µm or more and 500 µm or less.

The number of cell layers constituting the cell structure may be in the range of 2 or more and 60 or less.

In the culture step, the culture may be performed for a period in the range of 3 days or more and 14 days or less.

In the culture step, the number of the exosomes may be $1 \times 10^3$ or more relative to the normal cells of $2 \times 10^6$.

A kit that assesses the possibility of cancerization according to a second aspect of the present invention includes a cell culture vessel and a cell structure that is formed from normal cells formed on the cell culture vessel and includes a vascular network structure.

According to the foregoing aspects of the present invention, it is possible to assess the possibility of cancerization in the subject as a cancer suspect by using a body fluid specimen such as blood. This allows less invasive assessment of cancerization of cells of the subject.

Obviously, numerous modifications and variations of the present invention are possible in light of the above teachings. It is therefore to be understood that within the scope of the appended claims, the invention may be practiced otherwise than as specifically described herein.

What is claimed is:

1. A method of assessing a possibility of cancerization, comprising:
    a) culturing a cell structure comprising normal cells and a vascular network structure in a presence of a biological specimen from a subject to form vessels;
    b) counting a number of cells in the vessels; and
    c) determining a possibility of cancerization in the subject based on a state of the vessels in the cell structure after the culturing,
    wherein the normal cells in the cell structure include endothelial cells and cells other than the endothelial cells such that an abundance ratio of the endothelial cells to the normal cells in the cell structure is in a range of 0.1% to 10.0%, the biological specimen is a body fluid specimen from the subject, a cell extract of cells from the subject, or a culture supernatant of cells from the subject, and the possibility of cancerization is determined as high in the subject when the number of cells forming the vessels in the cell structure is larger than a number of cells cultured in an absence of the biological specimen, or when the vascular network structure in the cell structure extends.

2. The method of claim 1, wherein the body fluid specimen is blood, blood serum, blood plasma, urine, buffy coat, saliva, semen, chest exudate, cerebrospinal fluid, tear fluid, phlegm, mucus, lymph, ascites, pleural effusion, amniotic fluid, bladder lavage fluid, or bronchoalveolar lavage fluid.

3. The method of claim 1, wherein the biological specimen comprises exosomes.

4. The method of claim 3, wherein the culturing is conducted with $1 \times 10^3$ or more of exosomes with respect to $2 \times 10^6$ of normal cells.

5. The method of claim 3, wherein the endothelial cells in the cell structure include at least one selected from the group consisting of vascular endothelial cells and lymphatic endothelial cells.

6. The method of claim 5, wherein the cells other than the endothelial cells in the cell structure include at least one selected from the group consisting of fibroblasts, neural cells, dendritic cells, macrophages, and mast cells.

7. The method of claim 5, wherein the cells other than the endothelial cells in the cell structure include fibroblasts, and a total number of the vascular endothelial cells and the lymphatic endothelial cells in the cell structure is in a range of 0.1% to 10.0% of a number of cells of the fibroblasts.

8. The method of claim 3, wherein the cell structure comprises a plurality of cell layers such that the cell layers are laminated.

9. The method of claim 3, wherein the abundance ratio of the endothelial cells to the normal cells in the cell structure is in a range of 0.1% to 5.0%.

10. The method of claim 3, wherein the normal cells in the cell structure include the endothelial cells and the cells other than the endothelial cells such that a ratio of the endothelial cells to the cells other than the endothelial cells in the cell structure is in a range of 0.25% to 1.5%.

11. The method of claim 1, wherein the endothelial cells in the cell structure include at least one selected from the group consisting of vascular endothelial cells and lymphatic endothelial cells.

12. The method of claim 11, wherein the cells other than the endothelial cells in the cell structure include at least one selected from the group consisting of fibroblasts, neural cells, dendritic cells, macrophages, and mast cells.

13. The method of claim 11, wherein the cells other than the endothelial cells in the cell structure include fibroblasts, and a total number of the vascular endothelial cells and the lymphatic endothelial cells in the cell structure is in a range of 0.1% to 10.0% of a number of cells of the fibroblasts.

14. The method of claim 1, wherein the cell structure has a thickness in a range of 5 μm or more and 500 μm or less.

15. The method of claim 1, wherein the cell structure includes 2 to 60 cell layers.

16. The method of claim 1, wherein the culturing is conducted for 3 to 14 days.

17. The method of claim 1, wherein the cell structure comprises a plurality of cell layers such that the cell layers are laminated.

18. The method of claim 1, wherein the cell structure comprises a plurality of cell layers formed such that the cell layers are laminated and that the vascular network structure is formed in the cell structure.

19. The method of claim 1, wherein the abundance ratio of the endothelial cells to the normal cells in the cell structure is in a range of 0.1% to 5.0%.

20. The method of claim 1, wherein the normal cells in the cell structure include the endothelial cells and the cells other than the endothelial cells such that a ratio of the endothelial cells to the cells other than the endothelial cells in the cell structure is in a range of 0.25% to 1.5%.

* * * * *